(12) United States Patent
Judson et al.

(10) Patent No.: US 8,137,266 B2
(45) Date of Patent: Mar. 20, 2012

(54) SURGICAL PORTAL APPARATUS WITH ARMATURE ASSEMBLY

(75) Inventors: Jared Alden Judson, Topsfield, MA (US); Kenneth Allen Focht, Needham, MA (US); Oivind Brockmeier, Somerville, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 511 days.

(21) Appl. No.: 12/125,143

(22) Filed: May 22, 2008

(65) Prior Publication Data

US 2008/0294186 A1 Nov. 27, 2008

Related U.S. Application Data

(60) Provisional application No. 60/931,806, filed on May 24, 2007.

(51) Int. Cl.
*A61B 1/00* (2006.01)

(52) U.S. Cl. .................................. 600/184; 604/167.06

(58) Field of Classification Search ............ 604/164.01, 604/264, 506, 167.06; 606/108, 184; 600/184
See application file for complete search history.

(56) References Cited

U.S. PATENT DOCUMENTS

| | | | |
|---|---|---|---|
| 4,943,280 A | 7/1990 | Lander |
| 5,127,909 A | 7/1992 | Shichman |
| 5,180,373 A | 1/1993 | Green et al. |
| 5,209,737 A | 5/1993 | Ritchart et al. |
| 5,342,315 A | 8/1994 | Rowe et al. |
| 5,360,417 A | 11/1994 | Gravener et al. |
| 5,397,314 A | 3/1995 | Farley et al. |
| 5,407,433 A | 4/1995 | Loomas |
| 5,484,418 A | 1/1996 | Quiachon et al. |
| 5,492,304 A | 2/1996 | Smith et al. |
| 5,549,565 A | 8/1996 | Ryan et al. |
| 5,603,702 A | 2/1997 | Smith et al. |
| 5,634,908 A | 6/1997 | Loomas |
| 5,657,963 A | 8/1997 | Hinchliffe et al. |
| 5,685,854 A | 11/1997 | Green et al. |
| 5,720,759 A | 2/1998 | Green et al. |

(Continued)

FOREIGN PATENT DOCUMENTS

EP 1348386 A1 * 10/2003

OTHER PUBLICATIONS

European Search Report dated Aug. 29, 2008, Application No. EP 08 25 1778.

(Continued)

*Primary Examiner* — Kathleen Sonnett
*Assistant Examiner* — Katherine M Shi (57) ABSTRACT

A surgical portal apparatus includes a portal housing, an elongated portal member connected to the portal housing and an armature assembly. The portal housing and the portal member have an axial bore for reception and passage of a surgical object. The armature assembly includes at least two arms disposed within the portal housing and an outer mount. The at least two arms extend at least radially inwardly and are adapted to move relative to the longitudinal axis from a rest position to an activated position during passage of the surgical object. The at least two arms are operatively connected whereby movement of a first arm causes corresponding movement of a second arm. The outer mount comprises a resilient material and is mounted to the at least two arms, and imparts a biasing force thereto toward the rest position.

17 Claims, 7 Drawing Sheets

U.S. PATENT DOCUMENTS

| | | | |
|---|---|---|---|
| 5,722,958 A | 3/1998 | Gravener et al. | |
| 5,727,770 A | 3/1998 | Dennis | |
| 5,752,970 A | 5/1998 | Yoon | |
| 5,820,600 A | 10/1998 | Carlson et al. | |
| 5,895,377 A | 4/1999 | Smith et al. | |
| 6,228,061 B1 | 5/2001 | Flatland et al. | |
| 6,383,160 B1 | 5/2002 | Madsen | |
| 6,458,103 B1 | 10/2002 | Albert et al. | |
| 7,025,747 B2 * | 4/2006 | Smith | 604/167.06 |
| 7,063,685 B2 | 6/2006 | Rome | |
| 2002/0072713 A1 | 6/2002 | Almond et al. | |
| 2003/0187397 A1 | 10/2003 | Vitali | |
| 2004/0064100 A1 | 4/2004 | Smith | |
| 2004/0082969 A1 | 4/2004 | Kerr | |
| 2005/0165281 A1 | 7/2005 | Ravikumar | |
| 2006/0020281 A1 | 1/2006 | Smith | |
| 2006/0047284 A1 | 3/2006 | Gresham | |
| 2008/0091144 A1 | 4/2008 | Moran et al. | |

OTHER PUBLICATIONS

European Search Report dated Sep. 4, 2008, Application No. EP 08 25 1791.

* cited by examiner

SURGICAL PORTAL APPARATUS WITH ARMATURE ASSEMBLY

CROSS REFERENCE TO RELATED APPLICATION

The present application claims the benefit of and priority to U.S. Provisional Application Ser. No. 60/931,806 filed on May 24, 2007, the entire contents of which are incorporated herein by reference.

BACKGROUND

1. Technical Field

The present disclosure relates to a surgical portal for accessing underlying body tissue to permit the introduction of surgical objects in conjunction with a medical procedure. More particularly, the present disclosure relates to a surgical portal including an armature assembly for facilitating the alignment of a surgical instrument with an axis of the surgical portal, to thereby assist in the maintenance of the seal about the instrument and/or the minimize lateral movement of the instrument within the portal.

2. Discussion of Related Art

Surgical portals are employed in various minimally invasive procedures including laparoscopic or endoscopic procedures. Such portals are inclusive of trocar cannulas, catheters, or, in the event of a minimally invasive hand assist procedures, hand access devices. Surgical portals typically incorporate a seal mechanism to form a fluid tight seal about an instrument or hand passed through the portal. The seal mechanisms, however, often are limited by their ability to sustain a seal when an instrument, particularly, a smaller diameter instrument, is moved off-axis relative to a central axis of the portal. Moreover, the seal mechanisms are also limited by their ability to sustain their integrity when the surgical instrument is angulated. Such extreme ranges of motion of smaller diameter surgical instruments within the portal can create a "cat eye" or crescent shaped gap about the instrument resulting in fluid loss (e.g., insufflation gas loss).

SUMMARY

Accordingly, the present disclosure is directed to a surgical portal apparatus including a portal housing, an elongated portal member connected to the portal housing and depending therefrom and an armature assembly. The portal housing and the portal member have an axial bore for reception and passage of a surgical object. The armature assembly includes at least two arms disposed within the portal housing and an outer mount. The at least two arms extend at least radially inwardly and are adapted to move, e.g., pivotally move, relative to the longitudinal axis from a rest position to an activated position during passage of the surgical object. The at least two arms are operatively connected whereby movement of a first arm causes corresponding movement of a second arm.

The outer mount comprises a resilient material and is disposed within the portal housing. The outer mount is mounted to the at least two arms and imparts a biasing force to the at least two arms toward the rest position thereof. The outer mount has inner portions defining a passage to permit passage of the surgical object. The at least two arms may be at least partially embedded within the outer mount or enclosed within the outer mount. The armature assembly may include a series of arms coaxially arranged about the central longitudinal axis. Adjacent arms of the armature assembly may be interconnected by a gear. The outer mount may define a generally tapered configuration, e.g., a frustum. The inner portions of the outer mount may be adapted to establish a substantial seal about the surgical object.

In another embodiment, a surgical portal apparatus includes a portal housing, an elongated portal member connected to the portal housing and depending therefrom, and an armature assembly. The portal housing and the portal member have an axial bore for reception and passage of a surgical object. The armature assembly includes a series of arms disposed relative to the portal housing and extending at least radially inwardly and coaxially arranged with respect to the longitudinal axis. The arms are adapted for pivotal synchronized movement from a rest position to an activated position during passage of the surgical object. An outer mount comprising a resilient material has the arms at least partially embedded therein. The outer mount is adapted to impart a biasing force to bias the arms toward the rest position thereof whereby the arms tend to urge the surgical object in general alignment with the longitudinal axis. The outer mount has inner portions defining a passage to permit passage of the surgical object. The arms may include a series of gears for operatively connecting adjacent arms. The outer mount may define a tapered configuration. The inner portions of the outer mount may be adapted to establish a substantial sealed relation with the surgical object. The outer mount defines a proximal surface with the arms extending from the proximal surface to contact the surgical object during passage through the outer mount. The armature assembly may be releasably mountable to the portal housing.

BRIEF DESCRIPTION OF THE DRAWINGS

Preferred embodiments of the present disclosure will be better appreciated by reference to the drawings wherein.

DETAILED DESCRIPTION OF THE EMBODIMENTS

The portal apparatus of the present disclosure is capable of accommodating objects of varying diameters, e.g., including instruments from about 4.5 millimeter (mm) to about 15 millimeter (mm), during a minimally invasive surgical procedure. Moreover, the portal apparatus contemplates the introduction and manipulation of various types of surgical objects or instrumentation adapted for insertion through a trocar and/or cannula assembly while maintaining a fluid tight interface about the instrumentation to prevent gas and/or fluid leakage from the established pneumoperitoneum so as to preserve the atmospheric integrity of a surgical procedure. Specifically, the portal apparatus includes an armature assembly which while permitting angular manipulation of the surgical instrument normally biases the instrument into an aligned position with respect to the axis of the cannula. This feature of the present disclosure desirably minimizes the entry and exit of gases and/or fluids to/from the body cavity. Moreover, in one embodiment, the armature assembly provides a seal about the inserted instrument.

Examples of instrumentation contemplated for use with the portal apparatus include clip appliers, graspers, dissectors, retractors, staplers, laser probes, photographic devices, endoscopes and laparoscopes, tubes, and the like. Such instruments will be collectively referred to herein as "instruments or instrumentation".

In the following discussion, the term "proximal" will refer to the portion of the portal apparatus nearest to the clinician during operation while the term "distal" will refer to that portion of the portal apparatus most remote to the clinician.

Figures 1, 2:
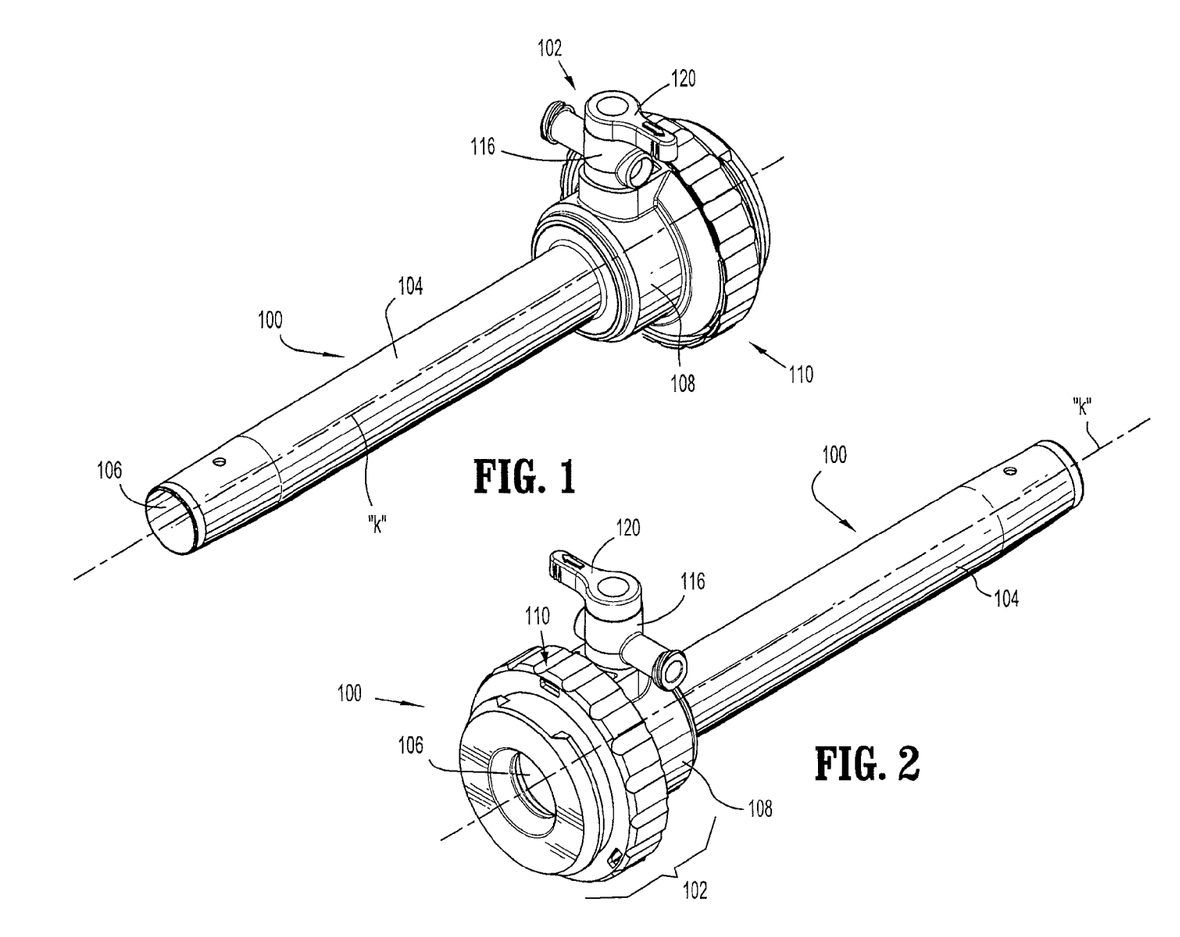
FIGS. 1-2 are perspective views of the surgical portal apparatus in accordance with the principles of the present disclosure.

Referring now to the drawings, in which like reference numerals identify identical or substantially similar parts throughout the several views, FIGS. 1-2 illustrate the portal apparatus 100 of the present disclosure. Portal apparatus 100 may be any member suitable for the intended purpose of accessing a body cavity and typically defines a passageway permitting introduction of instruments or the clinician's hand therethrough. Portal apparatus 100 is particularly adapted for use in laparoscopic surgery where the peritoneal cavity is insufflated with a suitable gas, e.g., $CO_2$, to raise the cavity wall from the internal organs therein. Portal apparatus 100 is typically used with an obturator assembly (not shown) which may be blunt, a non-bladed, or a sharp pointed instrument positionable within the passageway of the portal apparatus 100. The obturator assembly is utilized to penetrate the abdominal wall to introduce the portal apparatus 100 through the abdominal wall, and then subsequently is removed from the portal apparatus 100 to permit introduction of the surgical instrumentation utilized to perform the procedure through the passageway.

Portal apparatus 100 includes housing member 102 and portal member 104 connected to the housing member 102 and extending therefrom. Portal member 104 defines a longitudinal axis "k" extending along the length of the portal member 104. Housing member 102 and portal member 104 further define internal longitudinal passage 106 dimensioned to permit passage of surgical instrumentation. Portal member 104 may be formed of any suitable medical grade material, such as stainless steel or other rigid materials, including polymeric materials, such as polycarbonate, or the like. Portal member 104 may be transparent or opaque. The diameter of portal member 104 may vary, but typically ranges from about 4.5 millimeters (mm) to about 15 millimeters (mm).

Housing member 102 may include a number of components assembled together to define the outer housing shown in the drawings. For example, housing member 102 may include main housing 108 and armature assembly 110. Armature assembly 110 may or may not be a component of housing member 102. In one embodiment, armature assembly 110 may be selectively releasably mountable to main housing 108. In another embodiment, armature assembly 110 is an integral part of main housing 108. Armature assembly 110 will be discussed in greater detail hereinbelow. Main housing 108 is attached to the proximal end of portal member 104, specifically, to portal flange 112 of portal member 104. In one method, main housing 108 is connectable to portal flange 112 through a bayonet coupling, a threaded connection, snap fit, ultrasonic welding or any other means envisioned by one skilled in the art including, e.g., adhesive means. Additionally or alternatively, suture anchors may extend from main housing. Portal flange 112 and main housing 108 may be integrally formed with portal member 104.

Figure 3:
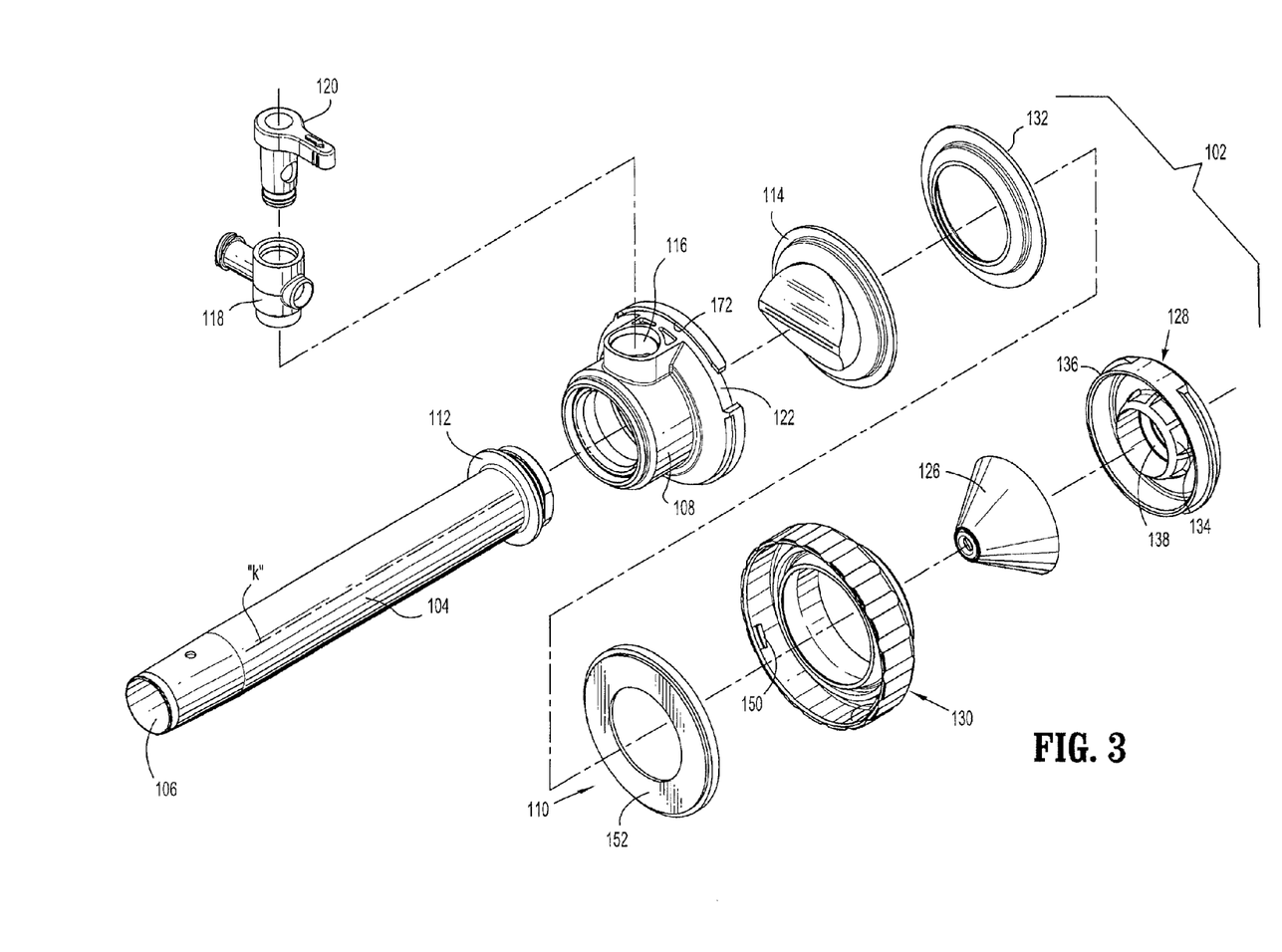
FIG. 3 is a perspective view with parts separated of the surgical portal apparatus of FIG. 1 illustrating the housing member, portal member, and armature assembly.
Figure 4:
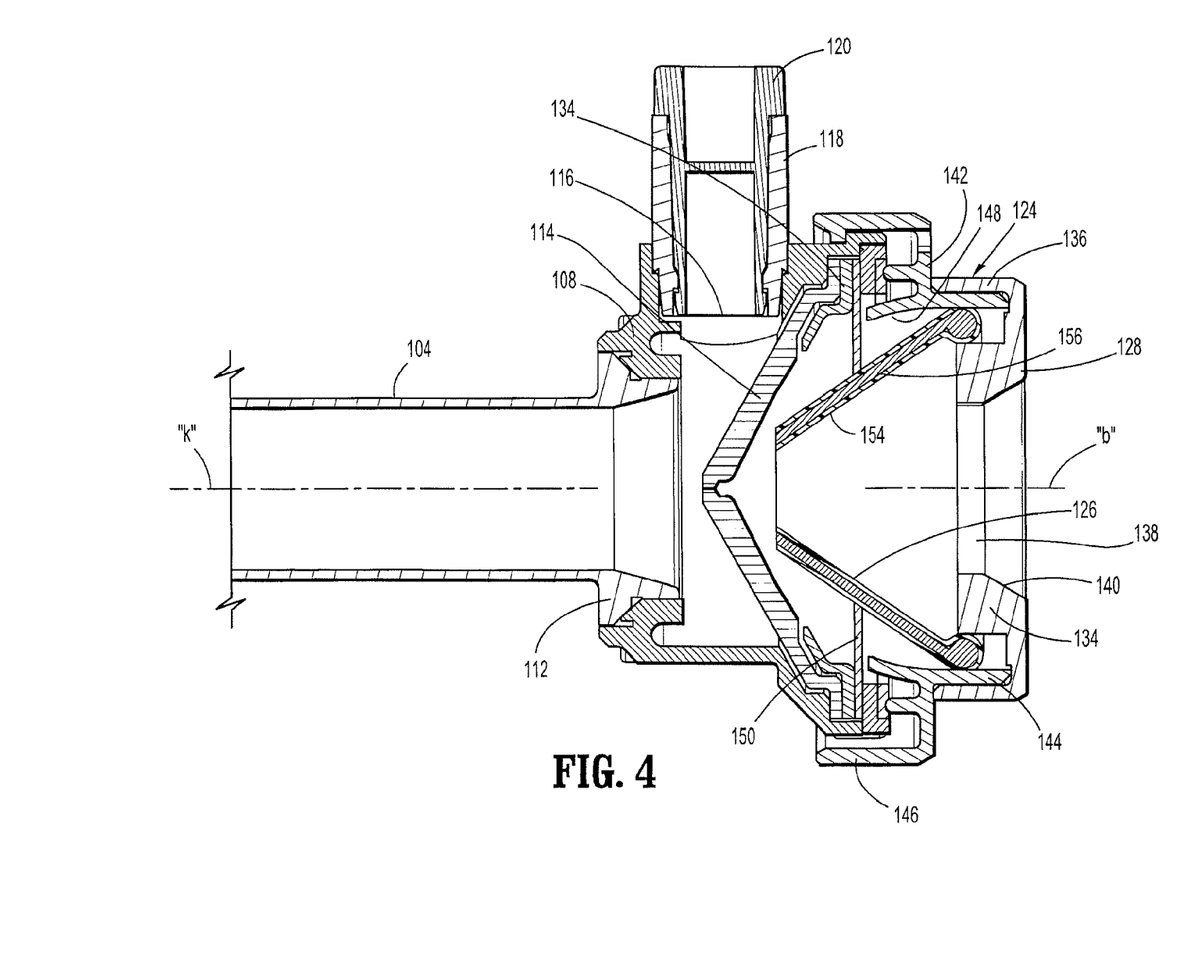
FIG. 4 is a side cross-sectional view of the housing member and the armature assembly.
Figure 5:
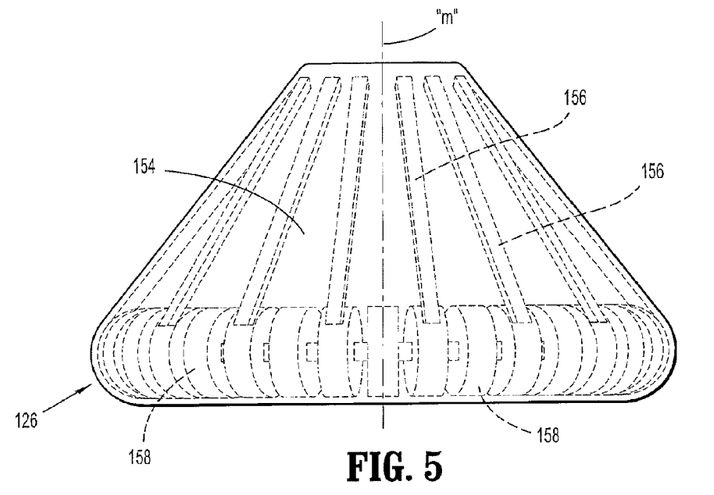
FIGS. 5 and 6 are side and top plan views respectively of the armature assembly illustrating the outer mount and the armature mechanism.
Figure 6:
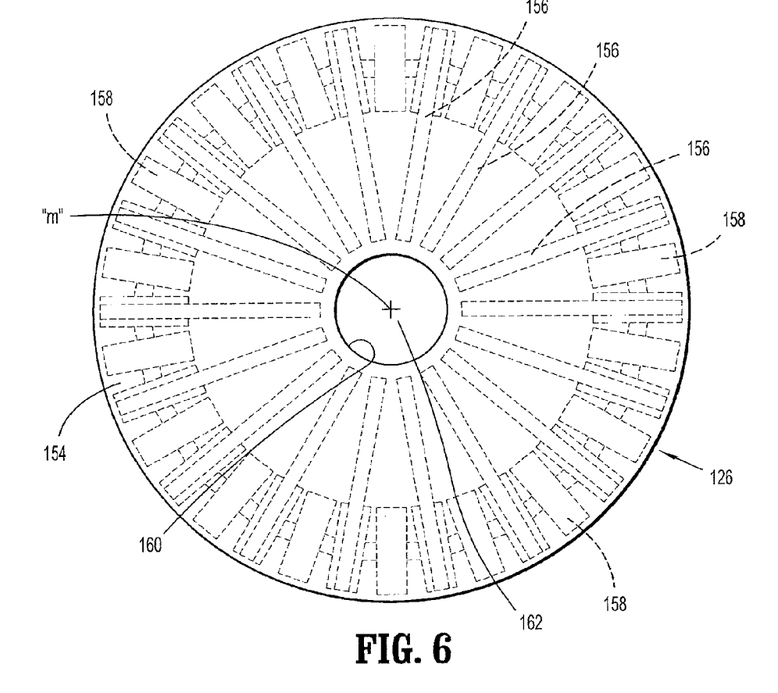
Figure 7:
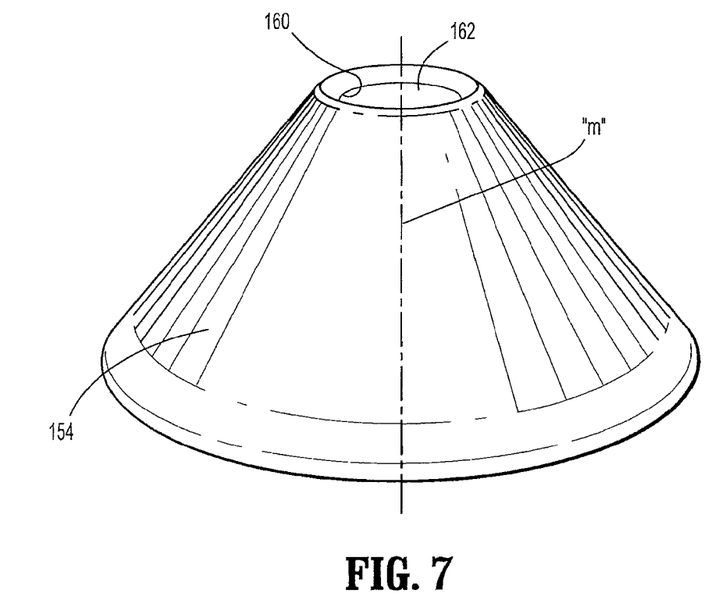
FIG. 7 is a perspective view of the outer mount of the armature assembly.
Figure 8:
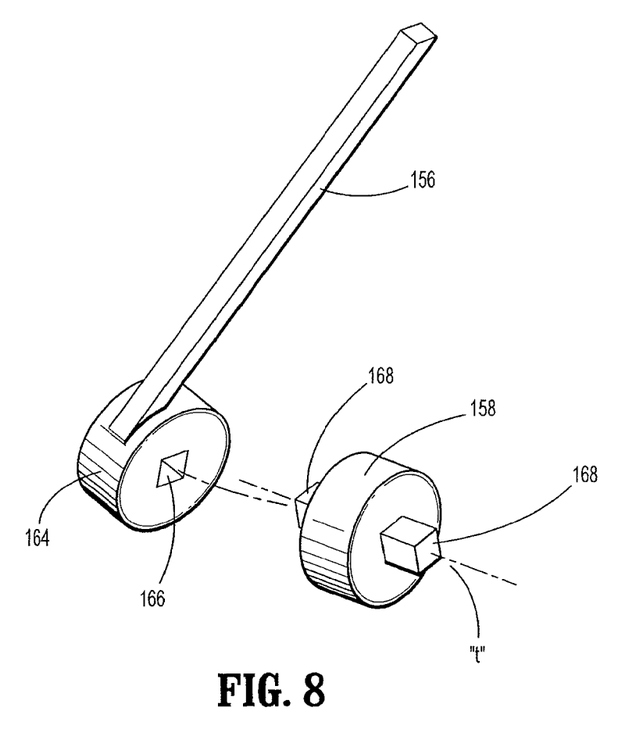
FIG. 8 is a perspective view of an arm and intermediate link of the armature mechanism.

Referring now to FIGS. 3-4, in conjunction with FIGS. 1-2, main housing 108 further includes valve 114. Valve 114 may be a zero-closure valve such as duck-bill valve having a slit which is adapted to close in the absence of a surgical object and/or in response to insufflation gases of the pressurized cavity. In the alternative, valve 114 may be a gel seal, balloon valve, or a flapper valve. Other zero closure valves are also contemplated including single or multiple slit valve arrangements, trumpet valves, flapper valves, or the like. Main housing 108 includes port opening 116 and luer fitting 118 positioned within the port opening 116. Luer fitting 118 is adapted for connection to a supply of insufflation gaseous is conventional in the art and incorporates valve 120 to selectively open and close the passage of the luer fitting 118. As best depicted in FIG. 3, main housing 108 includes at least one locking recess 122 preferably two recesses 122 arranged in diametrical opposed relation. Locking recesses 122 serve to releasably secure armature assembly 110 to main housing 108 of portal apparatus 100.

Referring now to FIGS. 3-4, armature assembly 110 will be discussed in detail. Armature assembly 110 may be a separate component from portal apparatus 100 and, accordingly, adapted for releasable connection to the portal apparatus 100. Alternatively, armature assembly 110 may be incorporated as part of portal apparatus 100. Armature assembly 100 includes armature housing, generally identified as reference numeral 124, and armature mechanism 126 which is disposed within the armature housing 124. Armature housing 124 defines central armature housing axis "b" which is preferably parallel to the axis "k" of portal member 104 and, more specifically, coincident with the axis "k" of the portal member 104. Armature housing 124 incorporates three housing components, namely, first, second and third housing components 128, 130, 132, respectively, which, when assembled together, form the armature housing 124. Assembly of housing components 128, 130, 132 may be affected by any conventional means.

First housing component 128 defines inner guide wall 134 and outer wall 136 disposed radially outwardly of the inner guide wall 134. Inner guide wall 134 defines central passage 138 which is dimensioned to receive a surgical instrument and laterally confine the instrument within armature housing 124. As best shown in FIG. 4, inner guide wall 134 defines sloped or tapered portion 140 adjacent its proximal end. Sloped portion 140 is obliquely arranged relative to housing axis "b" and extends radially inwardly relative to the housing axis "b" in the distal direction. Sloped portion 140 assists in guiding the inserted instrument into central passage 138, particularly, when the instrument is non-aligned or off-axis relative to the housing axis "b" or introduced at an angle relative to the housing axis "b". Sloped portion 140 provides more flexibility to the surgeon by removing the necessity that the instrument be substantially aligned with the housing axis "b" upon insertion.

Second housing component 130 includes transverse wall 142, inner cylindrical wall 144 depending in a proximal direction outwardly from the transverse wall 142 and outer wall 146 depending in a distal direction outwardly from the transverse wall 142. Inner cylindrical wall 144 is dimensioned to mate with outer wall 136 of first housing component 128, i.e., in a manner to be positioned within the interior of the outer wall 136 in frictional relation therewith. In the alternative, outer wall 136 of first housing component 128 may be adhered to inner cylindrical wall 144 of second housing component 130. Outer wall 146 defines scalloped outer surface which is dimensioned for gripping engagement by the user. Extending contiguously from inner cylindrical wall 144 in the distal direction is an arcuate or cup shaped wall support 148 which supports armature mechanism 126. Second housing component 130 may include internal locking detents 150 which serve to releasably secure armature assembly 110 to main housing 108.

Referring still to FIGS. 3-4, armature assembly 110 further includes interface seal 152 mounted adjacent armature assembly 126. Interface seal 152 functions in minimizing the loss of insufflation gases. Interface seal member 152 is preferably fabricated from an elastomeric material having qualities to engage outer surface of armature mechanism 126 in substantial sealed relation therewith. Third housing component 132 serves as the distal component in enclosing armature mechanism 126 within armature housing 124.

Referring now to FIGS. 5-8, in conjunction with FIG. 4, armature mechanism 126 will be discussed in detail. Armature mechanism 126 is mounted within armature housing 124 by any conventional means, including, e.g., through cooperation with wall support 148 of second housing component 130. For example, armature mechanism may be secured relative to wall support 148 and captured between wall support 148 and inner guide wall 134 of first housing component 128. Armature mechanism 126 may be secured within armature housing 124 in a manner to prevent longitudinal or radial movement of the entire armature mechanism 126, i.e., secured in fixed relation with armature housing 124. Armature mechanism 126 includes outer mount 154, a plurality or series of arms 156 coaxially arranged within outer mount 154 and intermediate gears or links 158 which interconnect adjacent arms 156. Outer mount 154 may be made of a molded elastomeric material and may define a tapered or frusto-conical configuration as shown. Other configurations for outer mount 154 are also envisioned. Suitable materials for outer mount 154 include polyisoprene or the like. Outer mount 154 further has inner portions 160 defining central aperture 162 which permits passage of the surgical instrumentation. In one embodiment, inner portions 160 are adapted to form a seal about the inserted instrument. In the alternative, inner portions 160 may permit passage of the instrument without forming a seal.

Arms 156 of armature mechanism 126 are preferably disposed within armature housing 124 and concentrically arranged with respect to the mount axis "m" of outer mount 154. Arms 156 extend both longitudinally and radially with respect to the mount axis "m" and portal axis "k". It is noted upon assembly of armature assembly 110 within main housing 108, mount axis "m", housing axis "b" and portal axis "k" are coincident with each other. In general, arms 156 are adapted to move, flex or pivot from the initial position depicted in FIGS. 5-8 to an activated position upon engagement of armature mechanism 126 with the inserted instrument. Arms 156 may be formed of a relatively rigid material, e.g., a material more rigid than the material of fabrication of outer mount 154, such as a rigid polymeric material or a metal including spring steel or the like. Arms 156 include gears 164 at one end. Gears 164 define polygonal opening or recess 166. Intermediate link 158 connecting adjacent arms 156 has a pair of correspondingly dimensioned teeth 168 which are received within polygonal openings 166 of arms 156 to operatively connect the adjacent arms 156. Accordingly, with this arrangement, any movement of one arm 156 causes corresponding rotational movement of intermediate link 158 and thus movement of a connected adjacent arm 156. In turn, this causes corresponding movement of the remaining arms 156 in the series as affected through the linkage mechanism provided by the intermediate links 158. Other means for operatively connecting arms 156 to move in synchronized manner are also envisioned such as the mechanism disclosed in commonly assigned U.S. Pat. No. 7,025,747B2 to Smith/Tyco Healthcare, the contents of which are incorporated herein by its entirety.

Arms 156 and intermediate links 158 are at least partially embedded within outer mount 154. In one embodiment, arms 156 and links 158 are fully embedded within outer mount 154. In one method of manufacture, outer mount 154 is overmolded onto arms 156 and intermediate links 158. Outer mount 154 may function to normally bias arms 156 and links 158 to the initial or rest position of FIG. 4 in which the distal ends of the arms 156 are positioned to intersect the passageway and engage the surgical instrument during insertion thereof. Thus, upon movement of arms 156 during engagement with a surgical instrument, the arms 156 bias the instrument to an aligned position with respect to the longitudinal axis "k".

The use of portal apparatus 100 in connection with introduction of a surgical instrument "i" will be discussed. Armature assembly 110 is mounted to main housing 108 if not an integral component of the housing member 102. In one method, the assembled armature assembly 110 is placed on main housing 108. Locking detents 150 of second housing component 130 are aligned with recesses 122 of main housing 108 to be received therein (FIG. 2). Armature assembly 110 is then rotated to cause locking detents 150 to engage an underside locking surface 172 of main housing 172 to thereby releasably secure armature assembly 110 to main housing 108.

Figure 9:
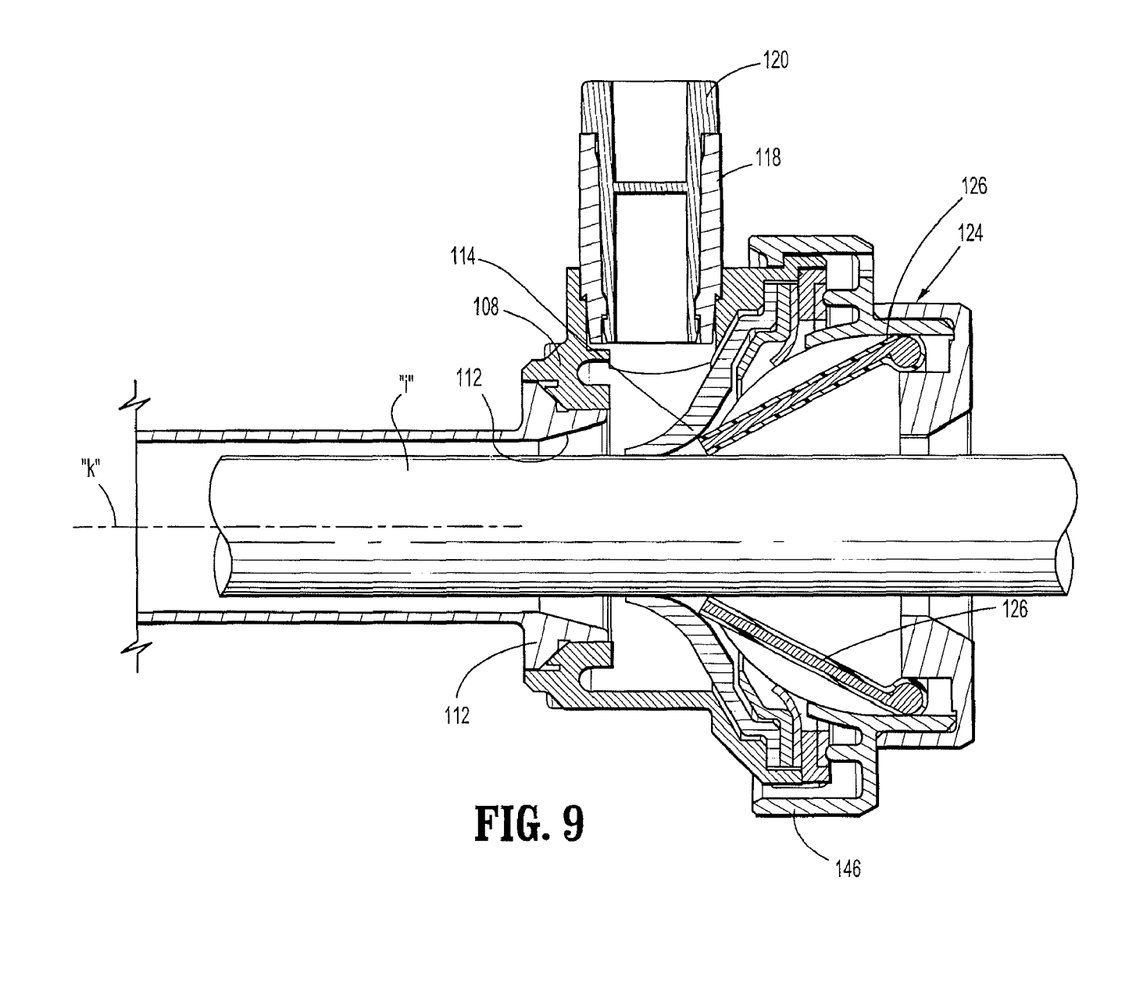
FIG. 9 is a side cross-sectional view similar to the view of FIG. 4 illustrating insertion of a surgical object through the housing member and the armature assembly.

Thereafter, portal apparatus 100 is introduced into an insufflated abdominal cavity typically utilizing a sharp or non-bladed obturator (not shown) positioned within longitudinal passage 106 of portal apparatus 100. The obturator is then removed leaving portal apparatus 100 to thereby define a portal to the underlying tissue within the abdominal cavity. With reference to FIG. 9, an object, e.g., a surgical instrument "i" is inserted into armature housing 124 and through armature mechanism 126. Simultaneous with the insertion of the instrument "i", at least one of arms 156 of armature mechanism 126 is engaged by the instrument "i" and initially moves, flexes or pivots in a radially outward direction relative to housing axis "b". This movement of arm 156 thereby causes adjacent connecting link 158 to rotate about its axis "t", which in turn causes an adjacent arm 156 to also rotate and move radially outwardly in synchronized manner to an activated position. Similarly, the remaining arms 156 are also caused to simultaneously or concurrently move. This simultaneous or concurrent movement functions to maintain or urge the inserted instrument "i" in general alignment with the axis "k" of the portal apparatus 100. In addition, during outward movement of arms 156, outer mount 154 is also stressed outwardly relative to mount axis "m" to assume a stressed, e.g., a stretched state. In this condition, outer mount 154 thereby applies a biasing force upon arms 156 to continually urge the arms 156 toward their initial position of FIG. 4. This also assists in capturing the instrument "i" between arms 156 and centering the instrument "i" with respect to axis "k". In addition, inner portions 160 of outer mount 154 may form a seal about the instrument introduced through aperture 162. Upon removal of the instrument "i", arms 156 return to their initial positions in response to the biasing effect of outer mount 154. Movement of arms 156 to the initial position is also synchronized as effected by the linkage mechanism.

Figure 10:
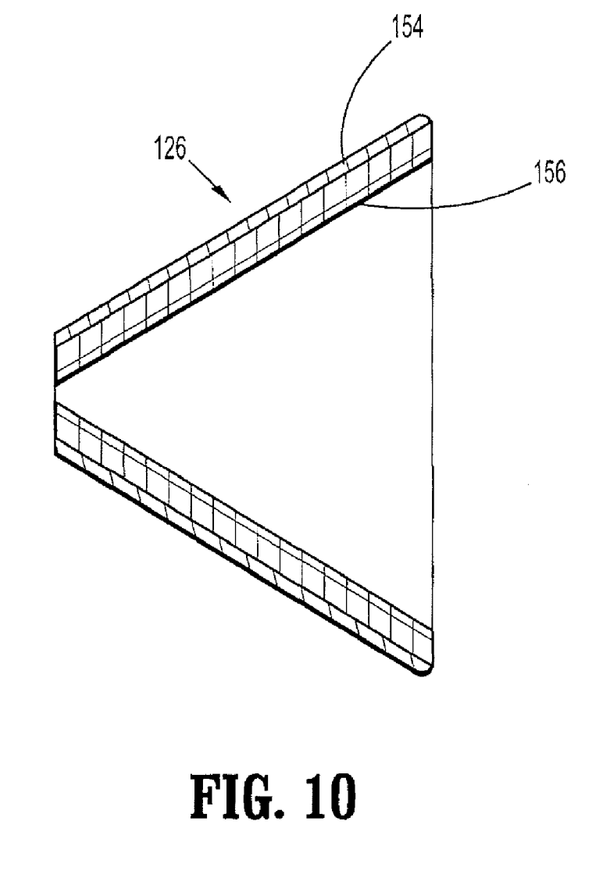
FIG. 10 is a side cross-sectional view of an alternate embodiment of the armature mechanism illustrating the arms extending from a proximal surface of the outer mount.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, arms 156 of armature assembly 110 may partially extend from a proximal surface of outer mount 154 as depicted in FIG. 10 to engage the instrument "i" upon insertion through armature assembly 110 thereby providing a degree of protection for the resilient material of the outer mount 154. Other variations are also envisioned.

What is claimed is:

1. A surgical portal apparatus, which comprises:
a portal housing;
an elongated portal member connected to the portal housing and extending therefrom, the portal member defining a central longitudinal axis, the portal housing and the portal member having an axial bore for reception and passage of a surgical object; and
an armature assembly including:
at least two arms disposed within the portal housing, the at least two arms extending at least radially inwardly and positioned to intersect the axial bore, the at least two arms dimensioned and adapted to move relative to the longitudinal axis from a rest position to an activated position during passage of the surgical object, the at least two arms being operatively connected whereby movement of a first arm causes corresponding pivoting synchronized movement of a second arm; and
an outer mount comprising a resilient material and being disposed within the portal housing, the outer mount having the at least two arms at least partially embedded within the resilient material thereof, the outer mount dimensioned and adapted to impart a biasing force to the at least two arms toward the rest position thereof, the outer mount having inner portions defining a passage to permit passage of the surgical object.

2. The surgical portal apparatus according to claim 1 including a series of arms coaxially arranged about the central longitudinal axis.

3. The surgical portal apparatus according to claim 2 wherein the outer mount defines a generally tapered configuration.

4. The surgical portal apparatus according to claim 3 wherein the outer mount defines a frustum.

5. The surgical portal apparatus according to claim 2 wherein adjacent arms are interconnected by a gear.

6. The surgical portal apparatus according to claim 1 wherein the inner portions of the outer mount are adapted to establish a substantial seal about the surgical object.

7. The surgical portal apparatus according to claim 1 wherein the at least two arms are enclosed within the outer mount.

8. The surgical portal apparatus according to claim 1 wherein the at least two arms are adapted to pivot between the rest position and the activated position.

9. The surgical portal apparatus according to claim 1 wherein the outer mount and the arms are dimensioned to form an integral structure.

10. The surgical portal apparatus according to claim 1 wherein the at least two arms are fully embedded within the resilient material of the outer mount.

11. A surgical portal apparatus, which comprises:
a portal housing;
an elongated portal member connected to the portal housing and depending therefrom, the portal member defining a central longitudinal axis, the portal housing and the portal member having an axial bore for reception and passage of a surgical object; and
an armature assembly including:
a series of arms disposed relative to the portal housing, the arms extending at least radially inwardly and coaxially arranged with respect to the longitudinal axis, the arms adapted for pivotal synchronized movement from a rest position to an activated position during passage of the surgical object; and
an outer mount comprising a resilient material and having the arms at least partially embedded within the resilient material thereof, the outer mount dimensioned and adapted to impart a biasing force to bias the arms toward the rest position thereof whereby the arms tend to urge the surgical object in general alignment with the longitudinal axis, the outer mount having inner portions defining a passage to permit passage of the surgical object.

12. The surgical portal apparatus according to claim 11 wherein the arms include a series of gears for operatively connecting adjacent arms.

13. The surgical portal apparatus according to claim 12 wherein the outer mount defines a tapered configuration.

14. The surgical portal apparatus according to claim 12 wherein the armature assembly is releasably mountable to the portal housing.

15. The surgical portal apparatus according to claim 11 wherein the inner portions of the outer mount are adapted to establish a substantial sealed relation with the surgical object.

16. The surgical portal apparatus according to claim 11 wherein the outer mount defines a proximal surface, the arms extending from the proximal surface to contact the surgical object during passage through the outer mount.

17. The surgical portal apparatus according to claim 11 wherein the series of arms are fully embedded within the resilient material of the outer mount.

* * * * *